United States Patent [19]

Webster

[11] 4,400,086

[45] Aug. 23, 1983

[54] INSTRUMENT FOR GRINDING AND ANALYZING MATERIAL IN GROUND STATE

[75] Inventor: Donald R. Webster, Laurel, Md.

[73] Assignee: Pacific Scientific Instruments Company, Anaheim, Calif.

[21] Appl. No.: 45,089

[22] Filed: Jun. 4, 1979

[51] Int. Cl.³ .......................... G01N 1/20; G01N 21/85
[52] U.S. Cl. ...................................... 356/36; 250/576
[58] Field of Search ................. 356/36, 440; 250/576; 73/421 B, 421 R

[56] References Cited

U.S. PATENT DOCUMENTS

| | | | |
|---|---|---|---|
| 2,668,470 | 2/1954 | Fischer | 356/36 |
| 3,679,312 | 7/1972 | Mansberg | 356/36 |
| 4,040,747 | 8/1977 | Webster | 356/418 |
| 4,171,916 | 10/1979 | Simms et al. | 356/366 |

Primary Examiner—William H. Punter
Attorney, Agent, or Firm—Lane, Aitken & Kananen

[57] ABSTRACT

In an instrument for optically measuring the constituents of grain samples, a grinder is provided to grind a sample of grain and direct the ground grain into a chute. A hopper is provided for loading the grain into the grinder with a gate for controlling the flow of the grain into the grinder. A filter wheel and infrared light source assembly directs a beam of infrared light on the grain sample in the chute while continuously changing the wavelength irradiating the grain. As the infrared light is irradiating grain, the grain is moved in a bed through the infrared light and reflectivity measurements are made. From these reflectivity measurements, the oil, water and protein content of the grain sample is determined.

7 Claims, 7 Drawing Figures

INSTRUMENT FOR GRINDING AND ANALYZING MATERIAL IN GROUND STATE

BACKGROUND AND SUMMARY OF THE INVENTION

In U.S. Pat. No. 4,040,747 to Donald R. Webster issued Aug. 9, 1977, there is disclosed a relatively low cost instrument for measuring and analyzing the optical properties of organic materials to determine the percentages of certain constitutents of the test materials. This instrument was developed to satisfy a need for a low cost instrument to rapidly determine the moisture, oil and protein content in produce and grain products. In the instrument disclosed in the patent, a source of wideband infrared light is positioned to illuminate a sample through a filter assembly in which interference filters are arranged in the form of a paddlewheel mounted for rotation about the axis. As the filter wheel rotates, each filter is brought successively into the infrared light beam. As each filter is moved through the light beam by the filter wheel, the angle of incidence of the light beam on the filter changes and this changes the wavelength transmitted through the filter. Thus, in this manner, a narrow band of wavelength irradiates the sample and the narrow wavelength is scanned over a wide range of wavelengths. Each filter provides a difference range of wavelengths. By detecting the amount of reflection at selected specific wavelengths and the relationships of these reflectivities, the oil, protein and water content of the sample can be accurately and quickly determined.

The most accurate measurements are obtained from the grain sample if the grain sample is first ground and the grinding should be carried out a short time before the measurement is made. This grinding operation increases the number of steps to make a measurement and also increases the amount of time and labor to make a grain sample measurement.

The present invention provides an instrument of the type disclosed in the Webster patent, but in which the grinding is carried out automatically in the instrument at the time the measurement is made. This eliminates the separate step of grain grinding normally employed in the prior art system disclosed in the Webster patent. Briefly, in accordance with the present invention, a filter wheel assembly is provided similar to that disclosed in the Webster patent. In addition, a grinding is provided on the instrument with a hopper to hold grain to introduce into the grinder. A plate blocks the bottom of the hopper from the grinder so that it may be filled with grain prior to a measuring operation. The instrument of the present invention, like that of the Webster patent, employs a reflectivity standard which is positioned in the path of the infrared rays prior to each measurement to automatically calibrate the instrument. To initiate operation of the instrument, the reflectivity standard is pivoted out of the path of the infrared light. This action automatically energizes the grinder motor. Then, after a two-second delay to permit the grinder motor to get up to speed, grain is permitted to flow from the hopper into the grinder and the ground grain flows into a chute, the bottom of which is arranged to receive the infrared light passing through the filter wheel. The bottom of the chute is closed by an impeller to remove the grain from the chute. After a delay of five seconds sufficient for the chute to fill up, the impeller is rotated to begin to move the grain out of the bottom of the chute. At this time, the instrument begins to make measurement as the grain in the chute moves through the infrared beam in the form of a ground bed of grain. This provides an automatic averaging from the sample being analyzed.

DESCRIPTION OF THE PREFERRED EMBODIMENT

Figure 1:
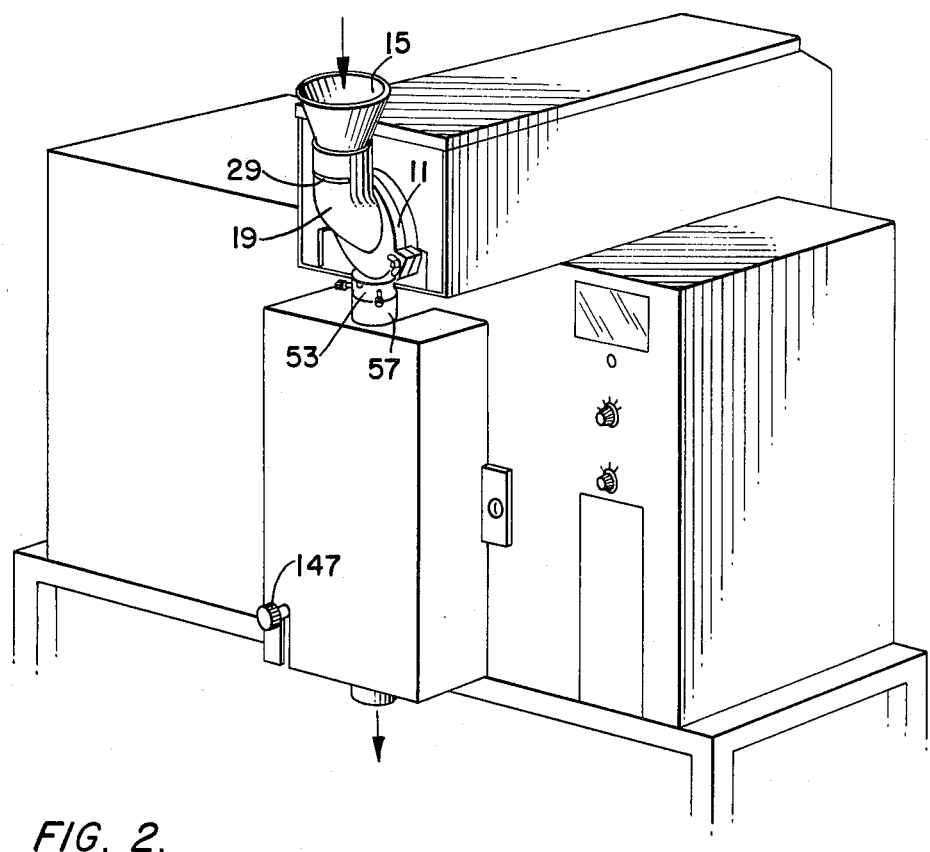
FIG. 1 is a perspective view of the grain analyzing instrument of the present invention.
Figure 2:
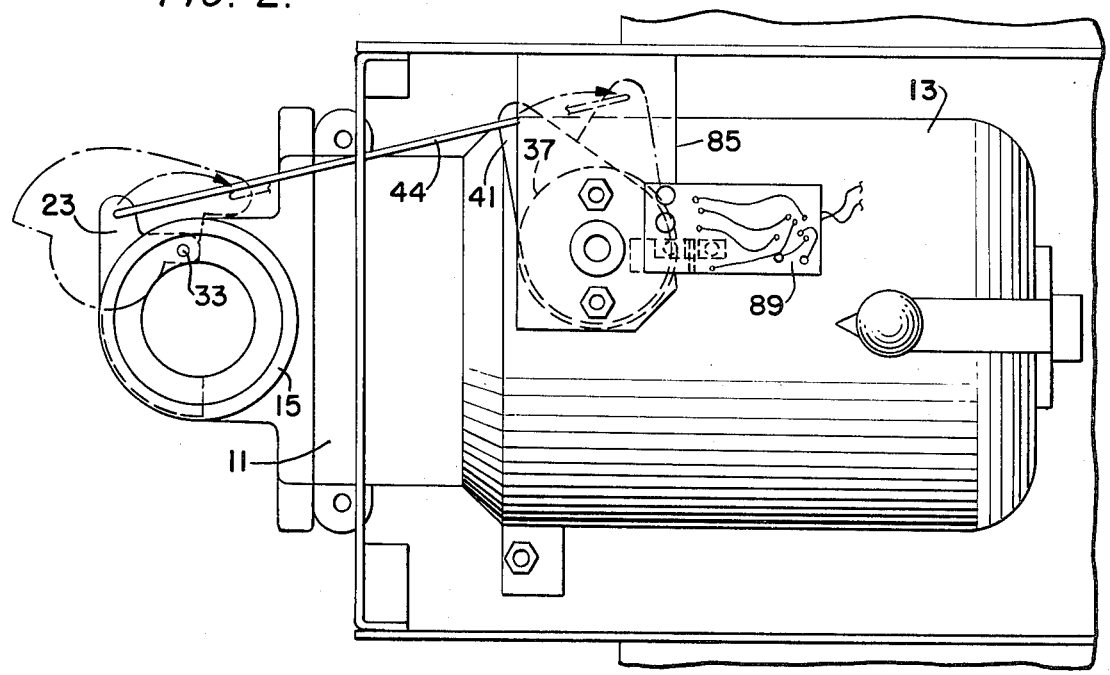
FIG. 2 is a top plan view of the instrument of the invention with the top cover over the grinder motor of the instrument of the invention removed.
Figure 3:
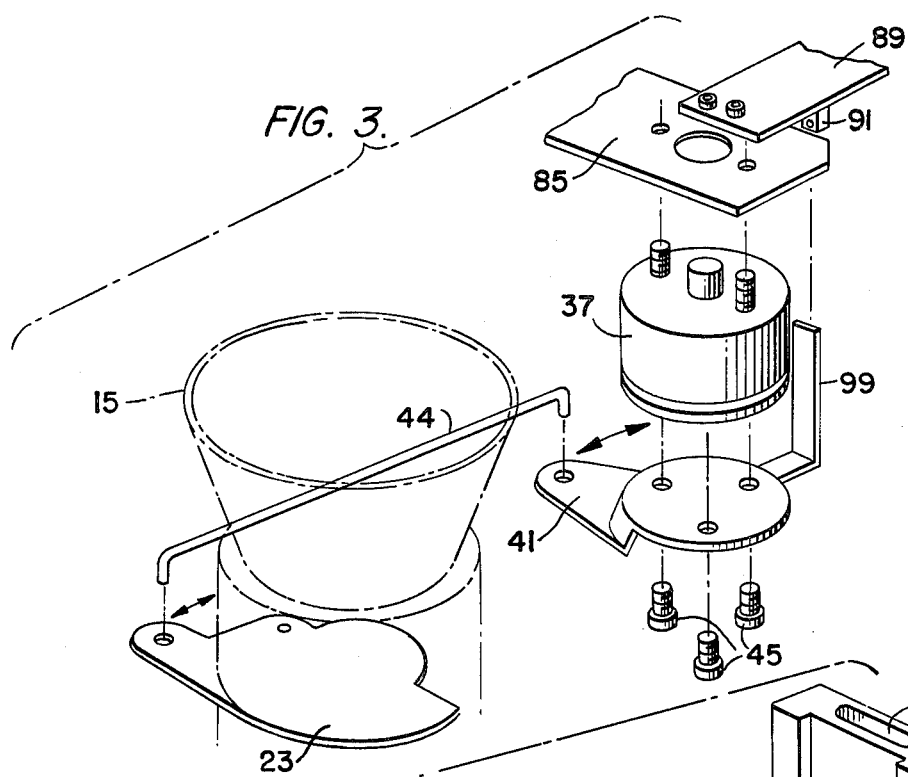
FIG. 3 is an exploded view showing the assembly of the grain hopper for loading grain into the grinder, the grain gate for controlling the flow of grain to the grinder and rotary solenoid controlling the positioning of the grain gate.

As shown in FIGS. 1-3, the grain analyzing instrument of the present invention comprises a grinder 11 which is driven by a motor 13 and is adapted to receive grain for grinding from a hopper 15. The hopper communicates with the input port to the grinder through a conduit 19, which can be selectively closed by a plate 23 pivoting in a slot 29 formed in the wall of the conduit 19. The plate 23, which is referred to as a "grain gate" pivots between the position shown in full lines in FIG. 2 and the position shown in phantom lines in FIG. 2. In the position shown in full lines, the grain gate blocks the conduit 19 and in the position shown in phantom lines, the grain gate leaves the conduit open. The pivoting of the grain gate 23 is controlled by a rotary solenoid 37 which rotates an arm 41 to pivot the grain gate 23 by means of a connecting rod 44 connected between the end of the arm 41 and the plate 23. As best shown in FIG. 3, the arm 41 is attached to the solenoid by screws 45.

Figure 4:
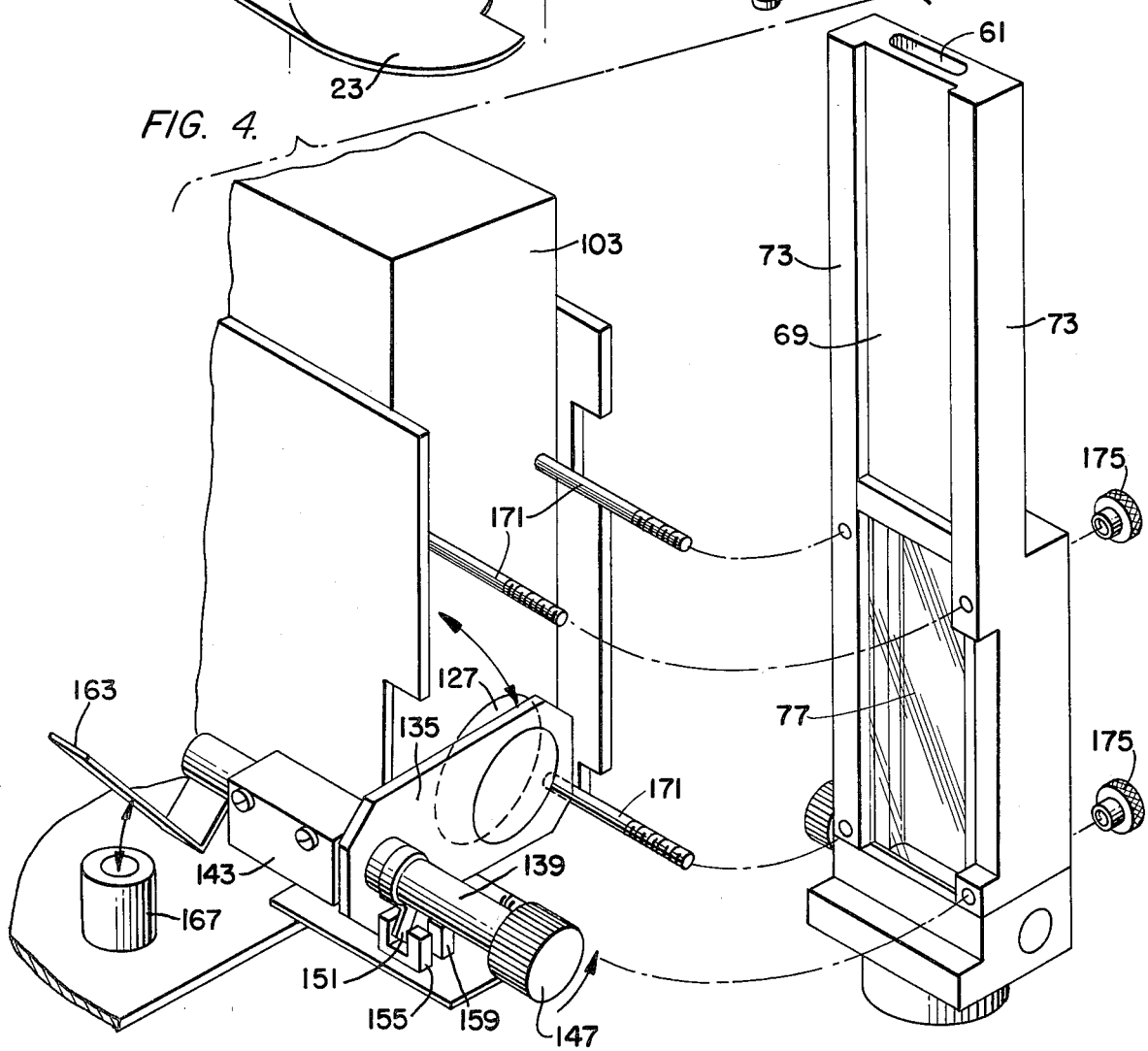
FIG. 4 is an exploded view showing the assembly of the chute for receiving ground grain from the grinder, a standard sample arm for calibrating the instrument and associated components.
Figure 5:
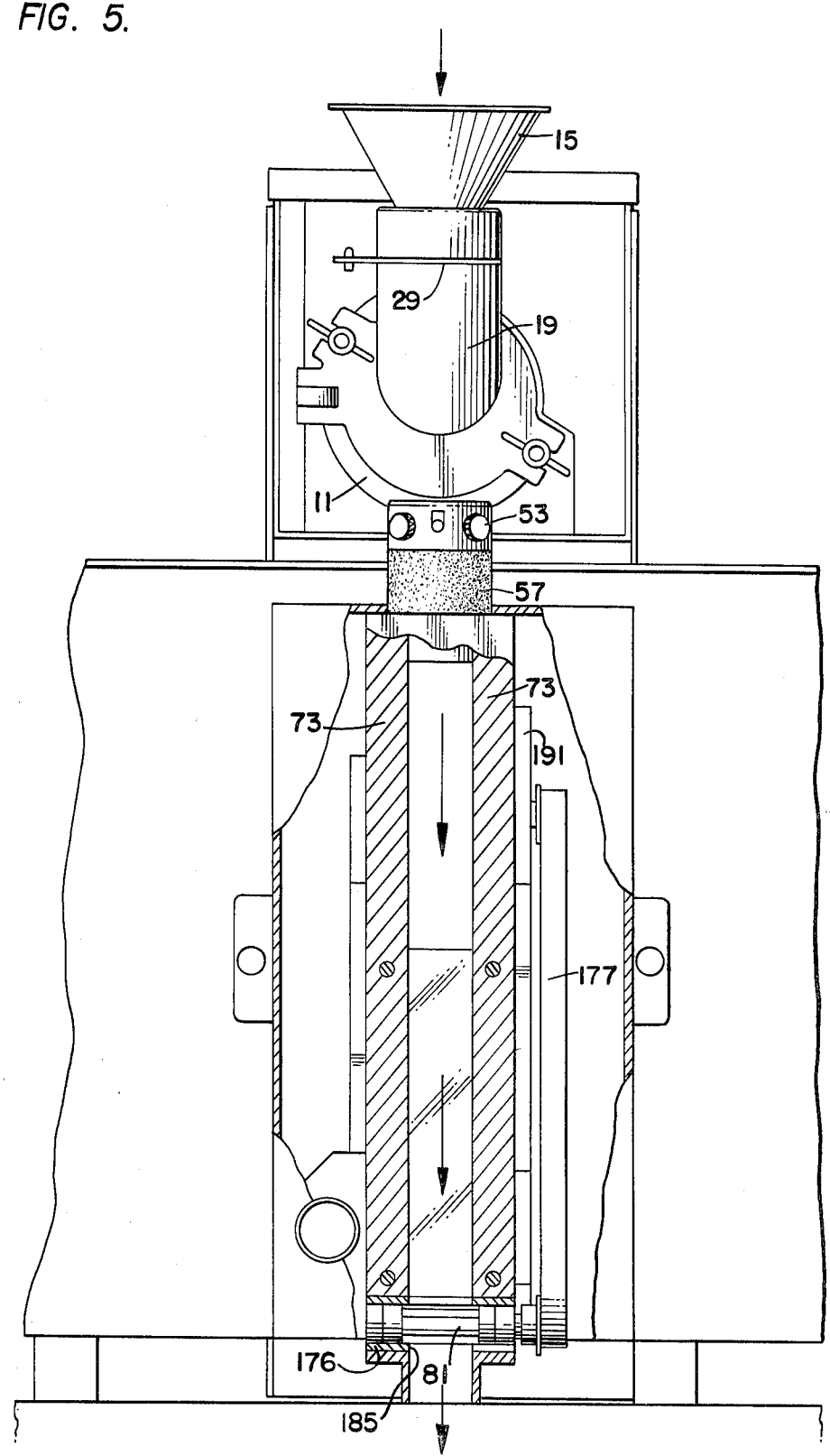
FIG. 5 is a front elevational view of the instrument of the invention shown partially in section through the chute for receiving the ground grain illustrating details of the chute and an impeller for removing grain from the chute.
Figure 6:
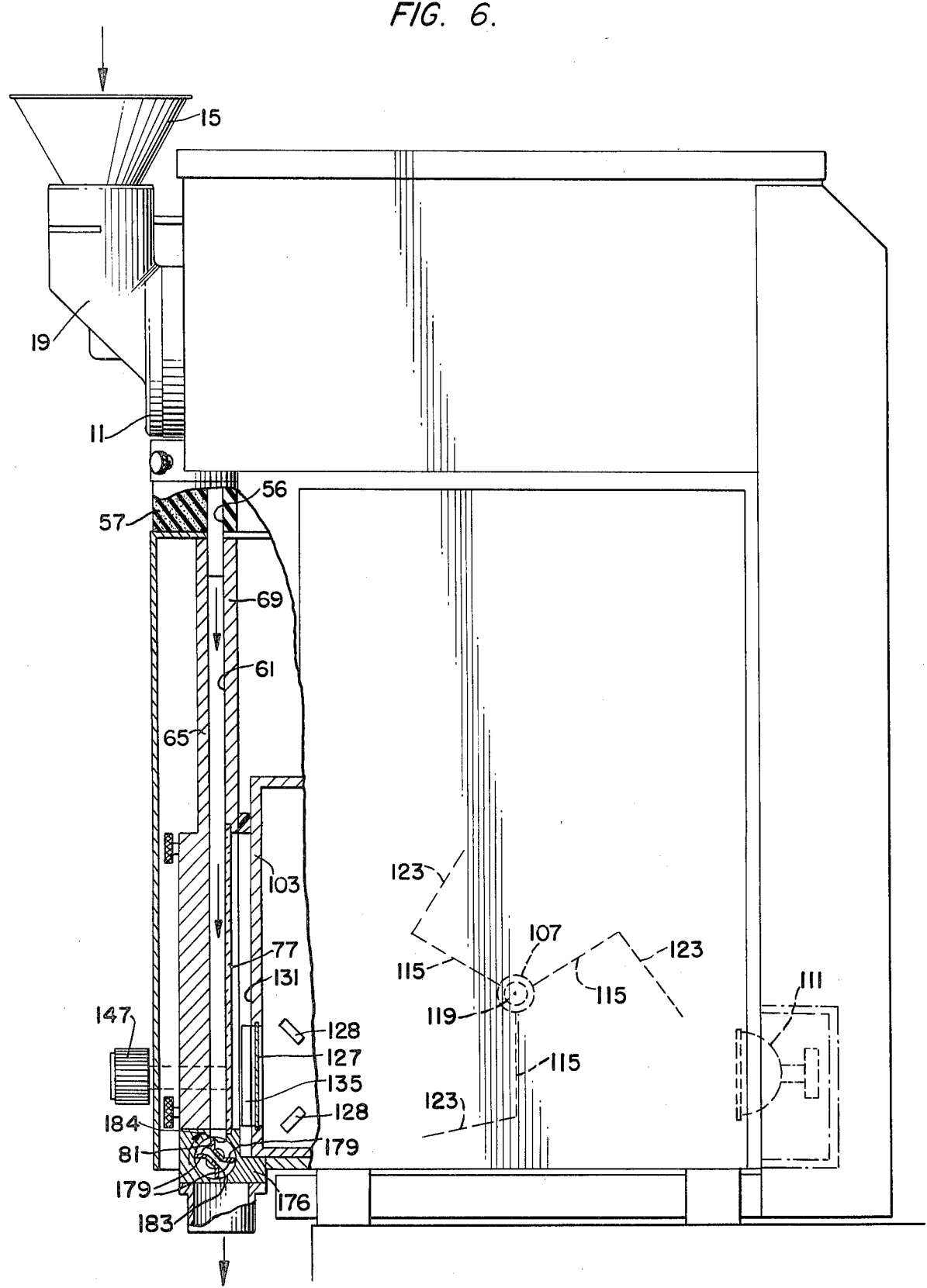
FIG. 6 is a side view in elevation of the instrument of the invention shown in partial section through the impeller mechanism.

As best shown in FIGS. 4-6, grain ground by the grinder 11 exits from the grinder through an exit port 53 at the bottom of the grinder and into a passageway 56 formed by a rubberized connector 57. The passageway 56 connects with a vertical chute 61 defined by front and back vertical walls 65 and 69 and sidewalls 73 to have a rectangular cross section. A window formed by an infrared light transmitting pane 77 is formed in the back wall 69 at the bottom of the chute 61. The bottom of the chute is closed by an impeller 81. The chute 61 together with the passageway 56 up to the exit port of the grinder are formed to define flush inner sidewalls or at least so that there are no ledges facing upward or against the direction of grain travel into the chute 61. This feature is important to avoid clogging of the instrument in operation.

As best shown in the exploded view of FIG. 3, the solenoid 37 is mounted on a bracket 85 which is fixed to the frame of the instrument. A printed circuit board 89 is mounted on the bracket 85 and a photodetector 91 is suspended below the printed circuit board 89. The rotary solenoid arm 41 has formed integral therewith an arm 99 which extends up to be detected by the photocell detector 91 when the grain gate 23 is in the position to block the channel in the conduit 19. The purpose of the photocell 91 is to provide a positive indication of when the grain gate is completely closed and positioned to block the conduit 19.

Contained within an inner casing 103 behind the window 77 is the filterhead assembly of the instrument which is the same as that disclosed in the issued U.S. Pat. No. 4,040,747 to Donald R. Webster. As disclosed in this patent, the filterhead assembly comprises a filter wheel 107 and a source 111 of infrared light. The filter wheel 107 comprises three interference infrared filters 115 extending out in a paddlewheel arrangement from a rotatable shaft 119. Attached to the outer end of each interference filter 115 is an opaque vane 123 extending at right angles to the filter. A window 127 is provided in the front wall of the inner casing 103 opposite the window 77. The infrared source directs an infrared beam through the window 127 toward the window 77 and the filter wheel 107 is arranged to rotate the filters into this beam of light so that the beam of infrared light passes through the three filters successively. In addition, the filter wheel continuously changes the angle of inclination of each filter as it passes through the beam of light to continuously change the narrow band of wavelength transmitted by each filter. The three filters are selected to each transmit a different range of wavelengths selected to detect by reflectivity the constituents's oil, water and protein in a grain sample. The opaque veins 123 periodically interrupt the beam of light for purposes of zeroing the instruments in the manner disclosed in the above mentioned U.S. Pat. No. 4,040,747.

As best shown in FIG. 6, there is a space 131 defined between the window 77 and the front wall 103 in which a standard arm 135 can pivot (see FIG. 4). Mounted on the back side of the arm 135 on the side adjacent to the wall 103 and window 127 is a porcelain disc (not shown). When the arm 135 is pivoted to the position shown in FIG. 4, the porcelain disc will be between the windows 127 and 77 and light from the source 111 after passing through window 127 will be reflected from the porcelain disc back through the window 127 to the photocells 128 positioned to detect light reflected back through the window 127. The porcelain disc serves as a standard of reflectivity to automatically calibrate the instrument in the manner described in the Webster U.S. Pat. No. 4,040,747, in which a Teflon disc is used as the standard of reflectivity. The porcelain disc serves the same purpose as the Teflon disc in the Webster patent.

The arm 135 can be pivoted upwardly as indicated by the arrow in FIG. 4 in which position the light from the source 111 after being filtered by the filter wheel 107 can pass through both windows 127 and 77 into the chute 61 to impinge upon grain in the bottom of the chute. The filtered infrared light will then be reflected back through windows 77 and 127 to the photocells 128. The arm 135, to be pivotable, is mounted on a shaft 139 which, in turn, is rotatably mounted in a bearing block 143. A knob 147 is mounted on the front end of the shaft 149 for rotating the shaft 139 and pivoting the arm 135. The knob 147, as shown in FIG. 1, extends through a slot in the front wall of the casing assembly of the instrument. Mounted on the shaft 139 is an arm 151 which moves between two photodetectors 155 and 159. In the position shown in FIG. 3, the arm 151 will be positioned to be detected by the photodetector 155 and in the upper position, the arm will be in position to be detected by the photodetector 159. On the back end of the arm 139, there is mounted a second arm 163 containing ferromagnetic material so as to coact with an electromagnet 167. When the arm 147 is pivoted to its upper position, energization of the electromagnet 167 will hold the arm 163 adjacent thereto and thus hold the arm 135 in its upper position. Then, when the electromagnet 167 is de-energized, the arm 135 will fall by gravity back to the position shown in FIG. 4, in which it is positioned between the windows 77 and 127.

As best shown in FIG. 4, the chute assembly comprising the front and back walls 65 and 69, the sidewalls 73 and the window 77 is mounted on the inner casing 103 by means of rods 171 which extend through the sidewalls of the chute assembly and are threaded on their outer ends to receive cap nuts 175 to secure the chute assembly in place and facilitate easy removal thereof.

The impeller 81 is mounted in a block 176 to be rotatable on its axis by means of a belt 177 driven by a motor 191 (FIG. 5). The impeller, as best shown in FIG. 6, comprises four blades 179 extending out from the axis of the impeller, the blades being formed from two plates 183 which are bent in a trough shape to form the four blades 179 as shown. The blades rotate in a cylindrical chamber 184 defined in the block 176. The bottom of the chute 61 extends through the top of the block 176 into the chamber 184 and a corresponding rectangular opening 185 is defined in the bottom of the block 176 communicating with the chamber 184. As the impeller 81 rotates in the chamber 184 with the bottom of the chute filled with ground grain, the impeller will remove the grain from the bottom of the chute and cause the grain to move across the window 77 in a continuous bed. In other words, the surface of the grain remains substantially undisturbed as it moves past the window 77.

To operate the system, the instrument is initially turned on in which condition a motor (not shown) will continuously drive the filter wheel 107 at a rate of six revolutions per second and the infrared source 111 will be directing a light beam through the filter wheel to the window 127. The arm 135 will be in position between the windows 127 and 77 so that the infrared beam will be reflected back from the porcelain standard to the photocells 128. In response to the resulting signal produced by the photocells 128, the instrument will be automatically calibrated in the manner described in the above mentioned Webster U.S. Pat. No. 4,040,747. Grain gate 23 will be closing off the conduit 19 and unground grain is loaded into the funnel 15. To initiate a measurement operation, the operator rotates the knob 147 to move the arm 135 to its upper position. This will initiate energization of the electromagnet 167 to hold the arm 135 in its upper position and, at the same time, initiate energization of the grinder motor 13. After a delay of two seconds selected to permit the grinder motor to get up to speed, the rotary solenoid 37 is energized to open the grain gate 23 and allow the grain to be fed to the grinder. The grinder will then begin to grind the grain and direct the ground grain into the chute 61. Then, after a delay of 5½ seconds selected to be sufficient to let the bottom of the chute fill up sufficiently with ground grain at least past the top of the window 127, the motor 191 will be energized to begin to drive the impeller 81. As a result, the impeller 81 will remove the ground grain from the bottom of the chute and cause the ground grain in the chute to move past the window 127 in a continuous bed. As the grain is being moved past the window 127, infrared light from the source 111 passing through the filters 115 of the filter wheel 107 will impinge upon the grain and be reflected to the photocells 128 and measurements of the constituents of the ground grain will be made in a manner described in the above mentioned Webster patent. After about 8 seconds, the measurement will be completed and the standard hold-up magnet 167 and the solenoid 37 will be de-energized. Accordingly, the standard arm 135 will fall back down between the windows 77 and 127 and the grain gate 23 will return to its closed position. Then, after another delay of 16 seconds selected to ensure that the grinder and chute are exhausted of the grain samples, the grinder will be de-energized and the grain removal motor is de-energized to return the system to a condition ready to make the next grain measurement.

Figure 7:
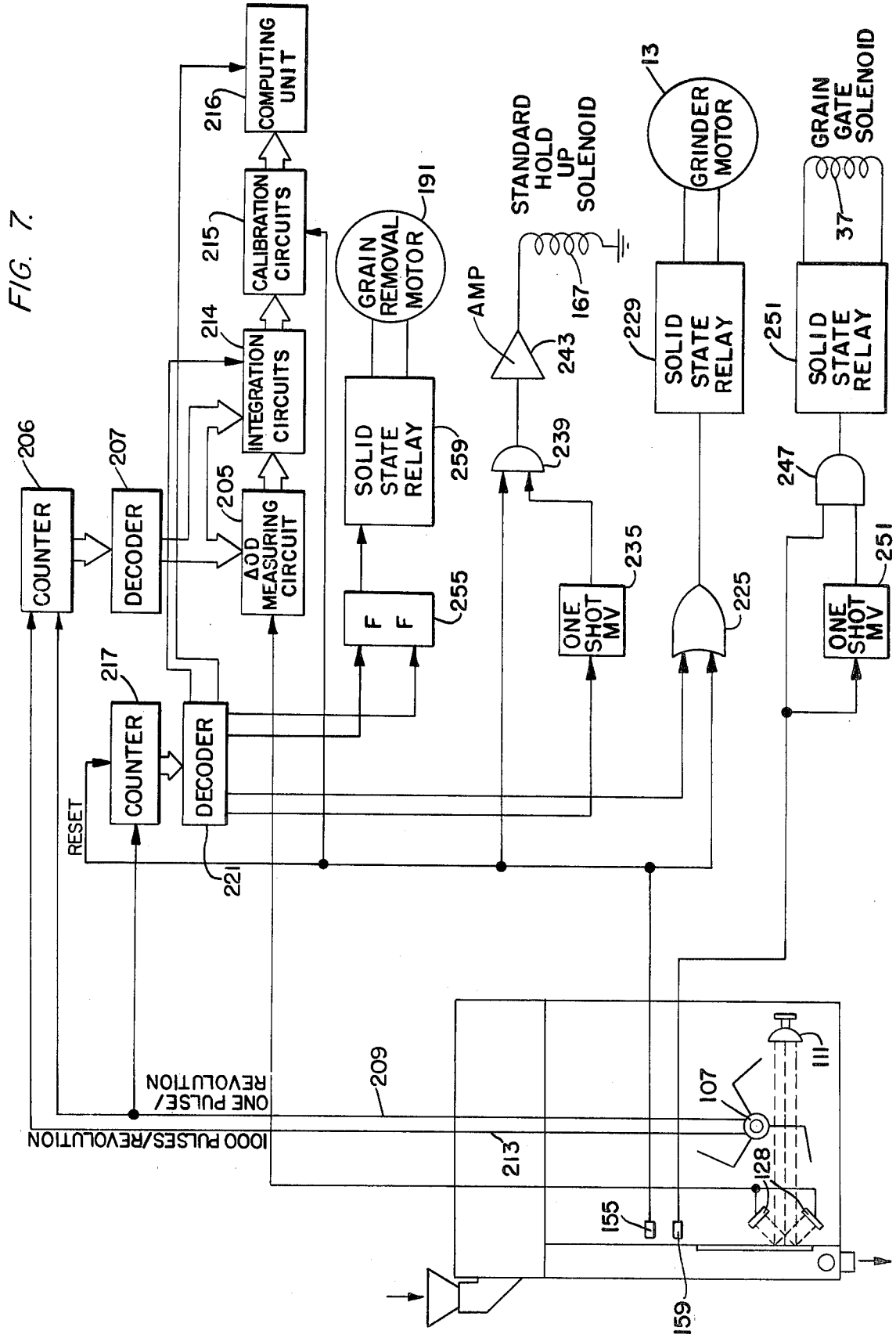
FIG. 7 is a schematic block diagram illustrating the electrical control system for controlling the sequence of operation of the instrument and schematically illustrating the electronic measuring system of the instrument.

As shown in the schematic illustration of FIG. 7, the filter wheel 107 produces pulses on channel 209 at a rate of one pulse per revolution of the filter wheel and the pulses on channel 213 at a rate of one thousand pulses per revolution of the filter wheel. The pulses on channel 209 are applied to a digital counter 205 to be counted thereby and signals from a digital counter are fed to a decoder 221, which generates control signals in response to the count in the counter.

When the standard arm 135 is pivoted out of its lower position, the resulting signal generated by the photodetector 155 is applied to the counter 217 to reset the counter to zero. The same signal generated by the photodetector 155 is also applied through an OR gate 225 to actuate a solid-state relay 229, which in turn energizes the grinder motor 13. The signal from the photodetector 155 is also applied as an enabling signal to an AND gate 239, which is connected to receive an enabling signal from a one-shot multivibrator 235 when the one-shot multivibrator 235 is in its untriggered state. When the AND gate 239 receives both enabling signals, the output thereof will be amplified by an amplifier 243 to energize the standard arm hold-up magnet 167. When the sample arm 135 is pivoted out of its lower position, the one-shot multivibrator will be in its untriggered state, so the standard arm hold-up magnet will be energized at this time. Thus, the standard hold-up magnet 167 will hold the standard arm 135 in its upper position when it is pivoted to this position. When the standard arm 135 has been pivoted to its upper position, the photodetector 159 will generate a signal which is applied as an enabling signal to an AND gate 247. The signal from the photodetector 159 will also trigger a one-shot 251 which, in its untriggered condition, applies an enabling signal to the gate 247. Two seconds after being triggered, the one-shot 251 will timeout and enable the gate 247 whereupon the output signal from the AND gate 247 will actuate a solid-state relay 251 to energize the grain gate rotary solenoid 37 and permit the grain, which has been loaded into the hopper, to flow to the grinder.

Five and one-half seconds after the counter 217 has been reset to zero, the count in the counter 217 will cause the decoder 221 to apply a signal to a flip-flop 255 which will then actuate a solid-state relay 259 to energize the grain removal motor 191. Accordingly, at this time, the grain removal motor will begin to drive the impeller 81 to cause the bed of ground grain to be advanced past the window 77. In this manner, the actuation of the impeller 81 is delayed to enable the chute to fill up sufficiently with grain before the impeller 81 is actuated. Thirteen and one-third seconds after the count in the counter 217 is set to zero, the count in the counter will cause the decoder 221 to disable the gate 239 whereupon the magnet 167 will be de-energized and the standard arm will be allowed to drop back down to its lower position. When the sample arm 135 drops back down, the photodetector 159 will no longer apply an enabling signal to the gate 247 and the grain gate solenoid will be de-energized to allow the grain gate to return to its closed position. In addition, the photodetector 155 will no longer be applying a signal to the solid-state relay 229 to cause it to energize the grinder motor. However, the decoder 221 will continue to apply a signal through the OR gate 225 to the solid-state relay 229 so that the grinder motor remains energized after the standard arm drops back down to its lower position to ensure that all of the grain loaded into the grinder is exhausted from the grinder. After another sixteen seconds, or a total of 29⅓ seconds, the count in the counter 217 will cause the decoder 221 to reset the flip-flop 255 whereupon the grain removal motor will be de-energized. At this same time, the decoder 221 will cease to apply a signal through the OR gate 225 to actuate the solid-state relay 229 so that the grinder motor 13 will also be de-energized.

During the period that the impeller 81 is rotated to withdraw the grain from the bottom of the chute so that a bed of grain is moving continously past the window 77, the bed of grain will be irradiated by the filtered infrared beam through the windows 127 and 77 and light will be reflected back to the photocells 128. The resulting signals generated by the photocells 128 are applied to a $\Delta$OD measuring circuit 205. The pulses on channels 209 and 213 are applied to a counter 206. The counter 206 counts the pulses on channel 213 and the pulses on channel 209 reset the counter 217 to zero to ensure synchronization of the counter with the rotation of the filter wheel. Signals from the counter 206 are applied to a decoder 207 which controls the $\Delta$OD measuring circuit 205 to make $\Delta$OD measurements for constituents in the grain samples in response to the signals received from photocells 128. The $\Delta$OD measuring circuit makes the $\Delta$OD measurements on the grain in the period starting immediately after the impeller 81 begins to draw grain from the bottom of the chute up to the time that the standard hold-up magnet 167 is de-energized allowing the standard arm to fall back down to its lower position so that the bed of grain is moving continuously through the beam of filtered infrared light while the $\Delta$OD measurements are being made.

The $\Delta$OD measuring circuit logarithmically amplifies the signal from the photocells 128 and applies the logarithmic signal to sample and hold circuits at appropriate times corresponding to selected wavelengths transmitted by the filter wheel 107. The decoder 207 enables the sample and hold circuits to store the applied signal from the logarithmic amplifier and then the difference between the stored signals at selected wavelengths is determined by a differential amplifier to provide ΔOD signals. The details of the ΔOD measuring circuit is fully disclosed in the Webster U.S. Pat. No. 4,040,747.

As explained in the above mentioned patent, ΔOD represents the difference in optical density at two characteristic wavelengths. Optical density, OD, refers to the ease with which light is transmitted through or reflected by an object. Reflective optical density is defined herein by the equation, $$OD = \text{Log}\,(1/R),$$

where R, reflectivity, equals the ratio of the intensity of reflected light to the intensity of incident light at a particular wavelength, $I_r/I_i$. Thus, $\Delta OD = \text{Log}\,(I_i/I_r)_1 - \text{Log}\,(I_i/I_r)_2$ in which the subscripts 1 and 2 indicate the two different wavelengths used for the measurement of ΔOD. If the intensity of incident light at both wavelengths is approximately the same, then $\Delta OD = -\text{Log}\,(I_r)_2 - \text{Log}\,(I_r)_1$. Thus, the ΔOD measuring circuit 205, in effect, provides a signal representing the difference between two logarithms of the intensity of reflected light at selected pairs of wavelengths. The measuring circuit in the preferred embodiment makes a separate ΔOD measurement for each of three pairs of wavelengths with the wavelengths for the ΔOD measurements being selected to measure the constituents water, oil and protein in the grain sample.

As the bed of grain moves across the window 77, the filter wheel will rotate several times and the ΔOD measurement for each selected pair of wavelengths will be measured several times, each of the three measurements being made once during each revolution of the filter wheel. The signals representing the ΔOD measurements are applied to integrating circuit 214 which is controlled by the decoder 207 to integrate corresponding successive ΔOD measurements made by the measuring circuit 205 to provide an average value for each of the three ΔOD measurements. This averaging is carried out as the bed of grain is moved past the window 77 and the reflective measurements taken. Thus, the ΔOD measurements are averaged over a surface area of the ground grain sample as the sample is moved through the filtered beam of infrared light.

The output signals from the integrating circuit 214 representing the average ΔOD values are applied to a calibration circuit 215 in which the average ΔOD values are automatically calibrated in accordance with the output readings from the photocells 128 taken from the porcelain standard prior to the reading taken from the grain. The calibration circuit 215 is controlled by the output signal from the photodetector 159 and performs calibration in the same manner as disclosed in the above mentioned U.S. Pat. No. 4,040,747. In effect, the calibration circuit as disclosed in the above mentioned patent makes the ΔOD measurements from the porcelain standard and then subtracts these ΔOD measurements from the ΔOD measurements which are made from the grain sample to provide the calibrated ΔOD values. The calibrated OD values then are applied to a computing unit 216 which determines the percentage of the oil, protein and water in the grain sample as disclosed in the above mentioned Webster patent.

The calibration circuit will begin to makes its calibration reading from the porcelain standard as soon as the standard arm 135 falls back down to its lower position. Thus, the instrument will be calibrated for the next grain sample during the 19-second time interval that he grinder 19 and the impeller 51 continue to run to exhaust the grain from the previous sample from the instrument after the sample arm 135 has fallen back to its lower position.

The above described instrument has been described as making measurements on grain samples. It will be apparent that te invention of the instrument can be applied to other grindable products to make analysis measurements. Other modifications may be made to the above described preferred embodiment of the invention without departing from the spirit and scope of the invention, which is defined in the appended claims.

I claim:

1. An analyzing instrument for analyzing grindable samples comprising a grinder for grinding said samples, a chute positioned to receive samples ground by said grinder, an impeller at the bottom of said chute for removing ground sample material from said chute, said chute having a window therein, measuring means to make optical measurements on the sample in said chute through said window while said impeller is removing the ground sample material from said chute, the interior walls of said chute being shaped so that there are no ledges in said chute facing in the opposite direction of the flow of ground sample material through said chute.

2. An analyzing instrument for analyzing grindable samples comprising a grinder for grinding said samples, a chute positioned to receive samples ground by said grinder, an impeller at the bottom of said chute for removing ground sample material from said chute, said chute having a window therein, measuring means to make optical measurements on the sample in said chute through said window while said impeller is removing the ground sample material from said chute, standard positioning means for positioning an optical standard in a first position for said measuring means to make said optical measurements on said optical standard and in a second position in which said measuring means makes said optical measurements on the ground sample in said chute, said measuring means including means to calibrate said measuring means in response to the optical measurements made on said optical standard, and means responsive to the movement of said standard positioning means from its first position to its second position to energize said grinder and then after a predetermined delay to actuate said impeller to remove ground sample material from said chute.

3. An instrument as recited in claim 2, wherein there is provided a hopper to receive a sample to be ground by said grinder, a conduit for feeding material of said sample to said grinder from said hopper, a gate for selectively blocking or unblocking said conduit, and means to activate said gate to unblock said conduit a predetermined delay after said grinder is energized, said last mentioned delay being shorter than said first mentioned predetermined delay.

4. An instrument as recited in claim 2, wherein said standard positioning means is manually moveable from said first position to said second position and is moveable by gravity from said second position to said first position, means responsive to the movement of said standard positioning means from said first position to said second position to magnetically hold said standard positioning means in second position and to release said standard positioning means to fall back to said first position after a predetermined delay longer than said first mentioned predetermined delay.

5. An instrument as recited in claim 4, wherein said measuring means includes means to irradiate said sample with light through said window and wherein said standard positioning means is operable to position said optical standard in said first position in front of said window in the path of said light.

6. An instrument as recited in claim 5, wherein said standard positioning means comprises an arm pivotable between said first and second positions and said optical standard is mounted on said arm near one end thereof.

7. An analyzing instrument as recited in any of claims 2-6, wherein the interior walls of said chute are shaped so that there are no ledges in said chute facing in the opposite direction of the flow of ground sample material through said chute.

* * * * *